United States Patent [19]

Williams

[11] Plant 4,923

[45] Nov. 9, 1982

[54] ROSE PLANT

[76] Inventor: Ernest D. Williams, 1510 Lebanon Ave., Dallas, Tex. 75208

[21] Appl. No.: 258,951

[22] Filed: Apr. 30, 1981

[51] Int. Cl.[3] ..... A01H 5/00

[52] U.S. Cl. ..... Plt./7

[58] Field of Search ..... Plt./7

*Primary Examiner*—Robert E. Bagwill

[57] ABSTRACT

The subject of this disclosure is a new and distinct variety of miniature rose primarily distinguished by the high centered exhibition form of its blooms and unique blending of the rose pink and white colors.

1 Drawing Figure

1

The present invention relates to a new and distinct variety of hardy, dwarf, bush type rose plant of the miniature class; the variety being primarily characterized — as to novelty — by near white (cream) buds and flowers with edges and tips of petals stippled pink to red, which in general color effect are similar to Toy Clown (miniature — U.S. Plant Pat. No. 2,903).

An abundance of bloom, with flowers usually borne one to the stem (sometimes several).

Some fragrance.

A plant which is vigorous, of rounded much branched shape with small matte foliage with pointed leaflets; the buds and flowers being similar in form and size to Over the Rainbow (miniature — U.S. Plant Pat. No. 3,472).

The plant, which has a normal height of 12–14 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between an unnamed seedling — as the seed parent, and Over the Rainbow (miniature — U.S. Plant Pat. No. 3,472) as the pollen parent.

Subsequent to origination of the variety I successfully asexually reproduced it in my nursery, located as aforesaid, by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; rounded; seedling; greenhouse; outdoors; cut flowers; garden decoration; potted plant.

Class: Miniature.

*Variety name.*—Charmglo.

Flowers borne: Singly and sometimes several together on slender wirey stems.

Quantity of bloom: Abundant both outside and in greenhouse.

2

Bud:

*Peduncle.*—Medium length; slender but sturdy; erect; medium green, sometimes tinted bronze (outdoors).

*Hairs.*—Usually several.

*Before calyx breaks.*—Size — small.

*Form.*—Pointed ovoid with several foliaceous appendages and numerous short hairs on surface of bud; with foliaceous parts extending beyond the tip of the bud equal to one-half or less of is length.

*Color.*—Medium green, occasionally tinted with bronze (outdoors).

*As calyx breaks.*—Color — near white often tinted or marked with pink.

*Opening.*—Opens well in all weather.

Bloom:

*Size when fully open.*—Small, averaging about $1\frac{1}{4}''$.

*Petalage.*—Double — averaging about 35 petals, arranged regularly plus sometimes a few small petaloids.

*Form.*—High centered at first, becoming more open in the center, with petals rolled loosely outward, and later at maturity open with petals rolled loosely outward and downward. Open flowers show stamens.

Petals:

*Fairly thick.*—Satiny on inside and on outside surface.

*Shape.*—Outside petals, broad lanceolate with very short acute (nearly round) tip; intermediate — broad lanceolate with very short acute or rounded tip; inside — lanceolate with short acute (nearly rounded) tip.

Color: Newly opened flower from a plant grown outdoors (August 1980), Dallas, Tex.:

*Outside petal.*—Outside surface — near white overlaid or flecked with rose pink near Rose Madder 23 (or lighter), on upper $\frac{1}{3}$ of petal. Inside surface — near white overlaid or flecked with rose pink, near Rose Madder 23/1 (or lighter) on upper $\frac{1}{3}$ (more or less) of petal.

*Intermediate petal.*—Outside surface — similar to outside petal. Inside surface — similar to outside petal.

*Inner petal.*—Outside surface same as intermediate petal; inside surface — same as intermediate petal.

*General color effect.*—Newly opened flowers — pink and white bicolor or blend varying with weather and time of year. Three days open — color similar to newly opened flowers, but with less pink. Behavior — opens well in all weather. Spent petals drop off. Flower longevity (September 1980) — plant in a pot 4–6 days or longer. Cut flowers at living room temperature 3–5 days or longer.

Reproductive organs:

*Stamens.*—Average number, arranged regularly about pistils.

*Filaments.*—Varying length, yellow.

*Anthers.*—Well formed; yellow.

*Pollen.*—Average.

*Pistils.*—Average number.

*Styles.*—Fairly even; medium length; bunched.

*Ovaries.*—All enclosed in calyx.

*Hips.*—Few or none.

*Sepals.*—Permanent; spear shaped; recurved.

*Seed.*—Few or none.

Foliage:

*Leaves.*—Compound of five (sometimes three) leaflets; quite small; leathery; matte.

*Leaflets.*—Shape: broad lanceolate; apex acute; base rounded, or rounded acute. Margin serrate. Color: medium green; new growth — normal (medium ) green. Rachis: medium strength; grooved; underside; several small thorns with some tiny hairs. Stipules: medium long; narrow to medium width; medium length; narrow points which turn out at about 45 degrees.

Growth:

*Habit.*—Dwarf; bushy; rounded; much branched.

*Growth.*—Free vigorous; internodes short.

*Canes.*—Medium; slender; sturdy.

*Main stems.*—Color: medium green.

*Thorns.*—Average; slender; hooked slighty downward; color — tan. Prickles — none. Hairs — none.

*Branches.*—Color: light to medium green. Thorns: average; short length; slender; hooked; color — greenish. Medium to short oval base. Prickles: none. Hairs: none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, much branched habit, substantially as illustrated and described, characterized by well shaped buds and flowers, the petals being near white overlaid or flecked with rose pink on upper $\frac{1}{3}$ (more or less) of the buds and flowers, resembling Over the Rainbow (miniature — U.S. Plant Pat. No. 3,472) in size and shape; and further characterized by a plant which is vigorous and compact, easy to propagate from cuttings, with an abundance of small matte foliage and an abundance of flowers borne singly or several to the stem.

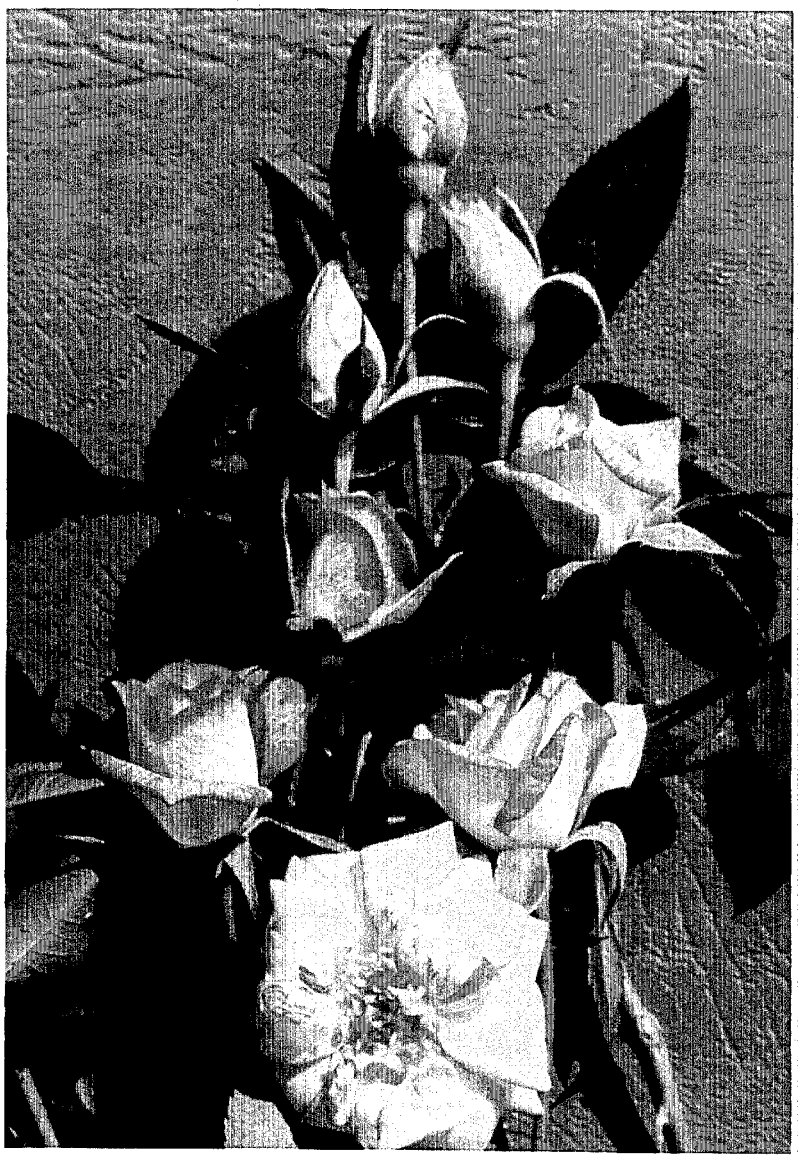

* * * * *